(12) United States Patent
Lu (10) Patent No.: US 12,387,299 B2
(45) Date of Patent: Aug. 12, 2025

(54) SYSTEMS AND METHODS FOR LOW-LIGHT IMAGE ENHANCEMENT

(71) Applicant: Stryker Corporation, Kalamazoo, MI (US)

(72) Inventor: Xudong Lu, West Vancouver (CA)

(73) Assignee: Stryker Corporation, Portage, MI (US)

( * ) Notice: Subject to any disclaimer, the term of this patent is extended or adjusted under 35 U.S.C. 154(b) by 518 days.

(21) Appl. No.: 17/561,660

(22) Filed: Dec. 23, 2021

(65) Prior Publication Data
US 2022/0207659 A1  Jun. 30, 2022

Related U.S. Application Data

(60) Provisional application No. 63/132,915, filed on Dec. 31, 2020.

(51) Int. Cl.
*G06T 5/73* (2024.01)
*G06T 5/50* (2006.01)

(52) U.S. Cl.
CPC ............ *G06T 5/73* (2024.01); *G06T 5/50* (2013.01); *G06T 2207/10068* (2013.01)

(58) Field of Classification Search
CPC ... G06T 5/73; G06T 5/50; G06T 2207/10068; G06T 5/90; G06T 2207/10016;
(Continued)

(56) References Cited

U.S. PATENT DOCUMENTS

| | | | |
|---|---|---|---|
| 7,850,598 B2 | 12/2010 | Kobayashi | |
| 9,182,347 B2 | 11/2015 | Ishihara | |

(Continued)

FOREIGN PATENT DOCUMENTS

| | | |
|---|---|---|
| JP | 3442653 B2 | 9/2003 |
| WO | 2019/103215 A1 | 5/2019 |

OTHER PUBLICATIONS

"Guang-Hao Ma et. al., Image Smoothing Based on Image Decomposition and Sparse High Frequency Gradient, May 2018, Journal of Computer Science and Technology 33[3], 502-210" (Year: 2018).*

(Continued)

*Primary Examiner* — Chineyere Wills-Burns
*Assistant Examiner* — Phuong Hau Cai
(74) *Attorney, Agent, or Firm* — Morrison & Foerster LLP (57) ABSTRACT

A method for enhancing low brightness regions in endoscopic video includes receiving a sequence of video frames captured during an endoscopic procedure. A brightness map is generated for each frame of the sequence of video frames. The brightness map is generated based on smoothing regional brightness in the respective frame based on regional brightness gradients. The brightness map for the respective frame includes scaling weights corresponding to pixels of the respective frame. An enhanced sequence of video frames is generated in real-time by adjusting pixel values of each frame of the sequence of video frames by scaling the pixel values of the respective frame by the scaling weights of the brightness map for the respective frame to enhance brightness of low brightness regions of the respective frame. The enhanced sequence of video frames is displayed in real-time.

29 Claims, 7 Drawing Sheets
(3 of 7 Drawing Sheet(s) Filed in Color)

(58) Field of Classification Search
CPC ........ G06T 2207/10024; H04N 23/555; H04N 23/741; A61B 1/000095; A61B 1/043; A61B 1/0669; A61B 1/07; A61B 1/042
See application file for complete search history.

(56) References Cited

U.S. PATENT DOCUMENTS

| | | | |
|---|---|---|---|
| 9,763,565 | B2 | 9/2017 | Homan |
| 10,080,485 | B2 | 9/2018 | Jang |
| 10,123,684 | B2 | 11/2018 | Sidar |
| 2011/0122241 | A1* | 5/2011 | Wang ............... H04N 7/185 382/128 |
| 2017/0046836 | A1 | 2/2017 | Bramwell et al. |

OTHER PUBLICATIONS

"Robert Haase et. al., CLIJ: GPU-accelerated image processing for everyone, Nov. 2019, Nature Methods 17, 5-6" (Year: 2019).*
"Raanan Fattal, Image Upsampling via Imposed Edge Statistics, Jul. 2007, SIGGRAPH 2007, pp. 95-es" hereinafter as "Fattal"). (Year: 2007).*
"Jiahao Pang et. al., Improved Single Image Dehazing Using Guided Filter, 2011, ASSIPA ASC 2011 Xi'an" (Year: 2011).*
"Humayun Kabir et. al., A Multilevel Compressed Sparse Row Format for Efficient Sparse Computations on Multicore Processors, Jun. 2015, 2014 21st International Conference on High Performance Computing, ISSN 1094-7256" (Year: 2014).*
"Deepak G. Skariah et. al., Nested Conjugate Gradient Algorithm with Nested Preconditioning for Non-Linear Image Restoration, Jun. 2017, IEEE Transactions on Image Processing, vol. 26, Issue 9" (Year: 2017).*
"Pablo Gomez et. al., Low-light Image Enhancement of High-Speed Endoscopic Videos using a Convolutional Neural Network, Mar. 2019, Medical & Biological Engineering & Computing vol. 57, pp. 1451-1463" (Year: 2019).*
"Pablo Gomez et. al., Low-light Enhancement of High-Speed Endoscopic Videos Using a Convolutional Neural Network, Mar. 2019, International Federation for Medical and Biological Engineering 2019, 57: 1451-1463" (Year: 2019).*
"Xiaojie Guo et. al., LIME: Low-Light Image Enhancement via Illumination Map Estimation, Feb. 2017, IEEE Transactions on Image Processing, vol. 26, Issue 2" (Year: 2017).*
Guo et al. (Feb. 2017). "LIME: Low-light Image Enhancement via Illumination Map Estimation," IEEE Transactions on Image Processing 26(2): 1-12.
International Preliminary Report on Patentability dated Jul. 4, 2023, directed to International Application No. PCT/US2021/073103; 7 pages.
International Search Report and Written Opinion mailed Mar. 18, 2022, directed to International Application No. PCT/US2021/073103; 11 pages.
Zhang et al. (May 4, 2019) "Kindling the Darkness: A Practical Low-light Image Enhancer," located at https://doi.org/10.48550/arXiv.1905.04161, (13 pages).
Office Action dated Feb. 11, 2025, directed to EP Application No. 21848509.2; 7 pages.

* cited by examiner

SYSTEMS AND METHODS FOR LOW-LIGHT IMAGE ENHANCEMENT

CROSS-REFERENCE TO RELATED APPLICATIONS

This application claims the benefit of U.S. Provisional Application No. 63/132,915, filed Dec. 31, 2020, the entire contents of which are hereby incorporated by reference herein.

FIELD

The present disclosure is related to medical imaging, and in particular, to image processing for medical imaging.

BACKGROUND

Minimally invasive surgery generally involves the use of a high-definition camera coupled to an endoscope inserted through a small incision into a patient to provide a surgeon with a clear and precise view within the body with minimal tissue damage. The endoscope emits light from its distal end to illuminate the surgical cavity and receives light reflected or emitted by tissue within the surgical cavity through a lens or window located at the distal end of the endoscope. Effectively illuminating the surgical cavity for imaging can be challenging. The confined nature of the surgical cavity and the unidirectional illumination provided by the endoscope often leads to inconsistent illumination of the surgical field. For example, regions closer to the distal end of the endoscope may be brightly illuminated while regions further from the distal end may be poorly illuminated. Poor illumination can lead to poor imaging, with detail of poorly illuminated regions being difficult to discern in the resulting imaging. Efforts to increase image brightness for poorly illuminated regions may cause problems for other regions. For example, increasing the level of illumination and/or increasing the camera gain may lead to oversaturation of regions that are more brightly illuminated.

SUMMARY

According to an aspect, systems and methods enhance low brightness regions in endoscopic video by generating on a frame-by-frame basis a brightness map that smooths regional brightness based on brightness gradients in an image and enhancing the respective frame by adjusting pixel values based on the brightness map. Pixel values associated with lower brightness regions are increased to a greater degree than pixel values associated with higher brightness regions such that lower brightness regions are enhanced without saturating higher brightness regions. The brightness map smooths regional brightness in regions of low brightness gradients while preserving brightness gradients in regions of high brightness gradients, which preserves detail in the frame. Optionally, the brightness map is generated in low scale space to reduce the processing time for providing frame-by-frame enhancement in real time.

According to an aspects, a method for enhancing low brightness regions in endoscopic video includes receiving a sequence of video frames captured during an endoscopic procedure; generating a brightness map for each frame of the sequence of video frames, wherein the brightness map is generated based on smoothing regional brightness in the respective frame based on regional brightness gradients; generating in real-time an enhanced sequence of video frames by adjusting pixel values of each frame of the sequence of video frames based on the brightness map for the respective frame to enhance brightness of low brightness regions of the respective frame; and displaying the enhanced sequence of video frames in real-time. It is noted that the method concerns the processing of endoscopic images. There is no functional link between the method and effects produced by the endoscope on the body. The endoscope can be pre-inserted into the body. The method can exclude the step of inserting the endoscope into the body. The method is not a method of treatment of the body.

Optionally, the enhanced sequence of video frames is generated in real-time by a graphics processing unit (GPU).

Optionally, the method includes down-sampling the respective frame and generating the respective brightness map based on the down-sampling of the respective frame. The method may include up-sampling the respective brightness map and adjusting the pixel values of the respective frame based on the up-sampling of the respective brightness map. The respective brightness map may be up-sampled using bilinear interpolation.

Optionally, generating the brightness map for each frame of the sequence of video frames includes minimizing a cost function, wherein the cost function comprises a sparse matrix and minimizing the cost function comprises constructing a compressed sparse matrix structure. The compressed sparse matrix structure may be constructed in compressed sparse row format. The compressed sparse matrix structure may include a row index vector, a column index vector, and a non-zero values vector, the row index vector and column index vector may be the same for each frame, and constructing the sparse matrix structure may include updating the non-zero values vector for the respective frame. An iterative conjugate gradient method may be used to solve the minimization of the cost function.

Optionally, the brightness map for the respective frame comprises a matrix of weights for pixels of the respective frame, wherein each weight is computed based on a brightness gradient of a corresponding region of pixels of the respective frame. Adjusting pixel values of each frame may include scaling the pixel values by the weights of the matrix of weights. Each frame may include different color channels and adjusting pixel values of each frame may include scaling each color channel of a given pixel by the same weight.

According to an aspect, a system includes one or more processors, memory, and one or more programs stored in the memory for execution by the one or more processors for: receiving a sequence of video frames captured during an endoscopic procedure; generating a brightness map for each frame of the sequence of video frames, wherein the brightness map is generated based on smoothing of regional brightness in the respective frame based on regional brightness gradients; generating in real-time an enhanced sequence of video frames by adjusting pixel values of each frame of the sequence of video frames based on the brightness map for the respective frame to enhance brightness of low brightness regions of the respective frame; and displaying the enhanced sequence of video frames in real-time.

Optionally, the enhanced sequence of video frames is generated in real-time by a graphics processing unit (GPU).

Optionally, the one or more programs include instructions for down-sampling the respective frame and generating the respective brightness map based on the down-sampling of the respective frame. The one or more programs may also include instructions for up-sampling the respective brightness map and adjusting the pixel values of the respective frame based on the up-sampling of the respective brightness map. The respective brightness map may be up-sampled using bilinear interpolation.

Optionally, generating the brightness map for each frame of the sequence of video frames includes minimizing a cost function, wherein the cost function comprises a sparse matrix and minimizing the cost function comprises constructing a compressed sparse matrix structure. The compressed sparse matrix structure may be constructed in compressed sparse row format. The compressed sparse matrix structure may include a row index vector, a column index vector, and a non-zero values vector, the row index vector and column index vector may be the same for each frame, and constructing the sparse matrix structure may include updating the non-zero values vector for the respective frame.

Optionally, the minimization of the cost function is solved via an iterative conjugate gradient method.

Optionally, the brightness map for the respective frame comprises a matrix of weights for pixels of the respective frame, wherein each weight is computed based on a brightness gradient of a corresponding region of pixels of the respective frame. Adjusting pixel values of each frame may include scaling the pixel values by the weights of the matrix of weights. Each frame may include different color channels and adjusting pixel values of each frame may include scaling each color channel of a given pixel by the same weight.

According to an aspect, a non-transitory computer readable medium includes instructions for execution by one or more processors for performing any one of the methods above. According to an aspect, a computer program product is provided comprising instructions which, when executed by one or more processors of a computer system, cause the computer system to perform any of the methods above.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The patent or application file contains at least one drawing executed in color. Copies of this patent or patent application publication with color drawing(s) will be provided by the U.S. Patent and Trademark Office upon request and payment of the necessary fee. The invention will now be described, by way of example only, with reference to the accompanying drawings, in which.

DETAILED DESCRIPTION

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

According to various aspects, systems and methods can provide brightness enhancement of images (single images or video frames) via a process that adjusts pixel values according to regional brightness. In some examples, a brightness map is generated for the image in which regions of low brightness gradients in the image are represented by regions of relatively uniform values, while the structure areas of strong gradients (e.g., edges) are preserved in the brightness map. The brightness map is used to scale the pixel values of the image, resulting in an enhanced image. In some examples, video frames are enhanced and techniques for reducing memory usage and processing time are used to enable real-time video frame (frame-by-frame) enhancement. In some examples, the image enhancement is performed on a GPU and parallel processing techniques are used to generate the brightness map. In some examples, the brightness map is generated by minimizing a cost function.

In some examples, one or more techniques are used to minimize memory usage and/or reduce processing time so that the brightness map and subsequent image enhancement can be performed in real-time. The brightness map can be generated based on an initial brightness map estimate generated from a respective frame and the initial brightness map estimate is down-sampled so that the cost function minimization problem involves a smaller data set, which can enable real-time video frame enhancement. The data set for the cost minimization problem can be stored in a compressed sparse matrix format, which reduces memory space and/or processing time. In some examples, the cost minimization problem is solved via an iterative conjugate gradient method utilizing a parallel processing platform, such as a graphics processing unit, to enable real-time solutions. The techniques for reducing memory storage and/or processing time may be critical for enabling real-time enhancement of video frames, in particular, for high definition video frames (e.g., 2K, 4K, or higher resolutions).

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining,"

"displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Figure 1:
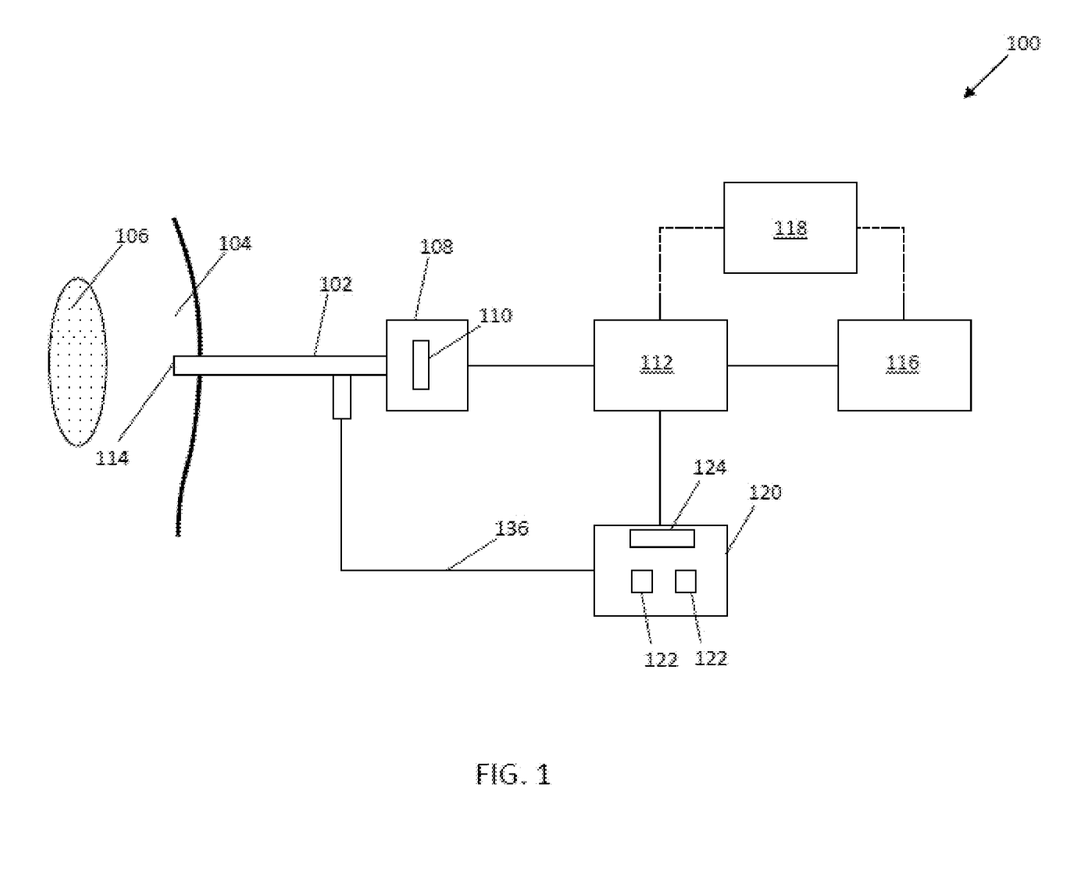
FIG. 1 is a block diagram of an exemplary endoscopic imaging system.

FIG. 1 illustrates an exemplary system 100 for endoscopic imaging. System 100 includes an endoscope 102 for insertion into a surgical cavity 104 for imaging tissue 106 within the surgical cavity 104 during a medical procedure and an illuminator 120 that provides illumination light to the endoscope 102, which emits the light from its distal end 114 for illuminating the tissue 106.

The endoscope 102 may extend from an endoscopic camera head 108 that includes one or more imaging sensors 110. As is well known in the art, light reflected and/or emitted (such as fluorescence light emitted by fluorescing targets that are excited by fluorescence excitation illumination light) from the tissue 106 is received by the distal end 114 of the endoscope 102. The light is propagated by the endoscope 102, such as via one or more optical components (for example, one or more lenses, prisms, light pipes, or other optical components), to the camera head 108, where it is directed onto the one or more imaging sensors 110. In some examples, one or more filters (not shown) may be included in the endoscope 102 and/or camera head 108 for filtering a portion of the light received from the tissue 106 (such as fluorescence excitation light).

The one or more imaging sensors 110 generate pixel data that can be transmitted to a camera control unit 112 that is communicatively connected to the camera head 108. The camera control unit 112 generates one or more images from the pixel data. As used herein "images" encompasses single images and video frames. In some examples, the images can be transmitted to an image processing unit 116 for further image processing, storage, display, and/or routing to an external device (not shown). The images can be transmitted to one or more displays 118, from the camera control unit 112 and/or the image processing unit 116, for visualization by medical personnel, such as by a surgeon for visualizing the surgical field 104 during a surgical procedure on a patient.

The illuminator 120 generates illumination light and provides the illumination light to the endoscope 102 via light guide 136, which may comprise, for example, one or more fiber optic cables, with the light guide 136 coupled to the endoscope 102 at the light post 126 in the proximal region of the endoscope. The illumination light is emitted from the distal end 114 of the endoscope 102 and illuminates the tissue 106. As used herein, "illumination light" refers to light that may be used to illuminate tissue for the purposes of imaging the tissue. In some examples, at least a portion of the illumination light may be light having a waveband in the visible spectrum that is reflected by the tissue 106 and captured by the one or more imaging sensors 110 for generating visible light imaging data. According to various examples and/or operating modes, at least a portion of the illumination light can be fluorescence excitation light for exciting one or more fluorescing targets in the tissue, which can include one or more fluorescence agents and/or one or more auto-fluorescing targets. Light emitted by the one or more fluorescence targets may be captured by the one or more imaging sensors for generating fluorescence imaging data. The illumination light can include any desirable wavebands or combination of wavebands.

The illuminator 120 includes one or more light sources 122 that each generate one or more wavebands of light and a controller 124 for controlling the light sources 122. The light sources 122 generate illumination light for illuminating the tissue 106 via the endoscope 102. The controller 124 can be configured to activate and deactivate the individual light sources 122 and/or adjust a power level of the light sources 122 to adjust the level of intensity (i.e., the luminance) of light generated by the individual light sources 122. In some examples, the controller 124 may control one or more light sources 122 based on one or more control signals received from camera control unit 112 and/or image processing unit 116. In some examples, control signals received from the camera control unit 112 and/or image processing unit 116 can instruct the controller 124 how to control individual light sources 122, such as by including instructions to activate or deactivate individual light sources 122 and/or to set one or more individual light sources 122 at a specified power/intensity level. For example, the camera control unit 112 and/or image processing unit 116 may determine that a specific color and/or intensity adjustment is needed based on analysis of pixel data generated by the endoscopic camera head 108 and the controller 124 may receive instructions specifying the adjustments.

Figure 2:
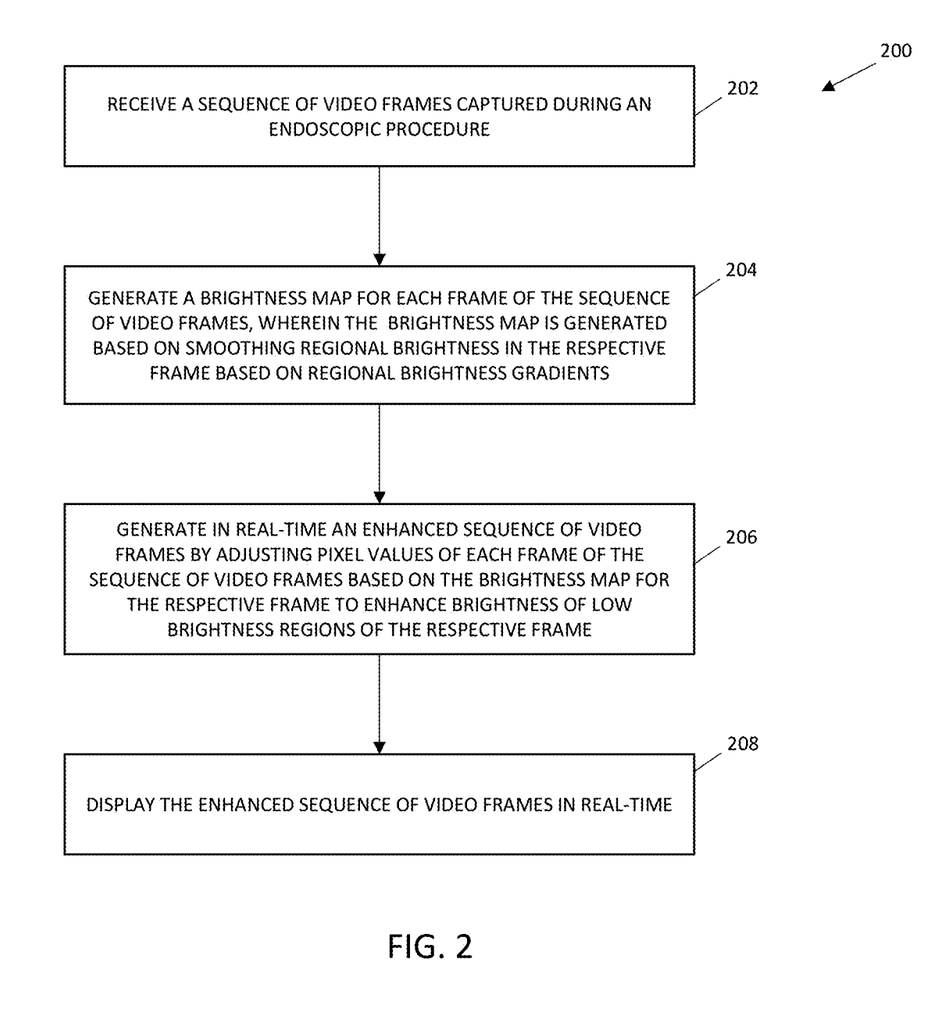
FIG. 2 illustrates an exemplary method for low-light image enhancement for endoscopic video imaging.

FIG. 2 illustrates an exemplary method 200 for low-light image enhancement for endoscopic video imaging. Method 200 can be performed by an endoscopic imaging system, such as system 100 of FIG. 1. For example, method 200 can be performed by an image processing unit, such as image processing unit 116 of FIG. 1. In some examples, method 200 or at least a portion of method 200 is performed by a GPU for real-time enhancement and display of video frames.

At step 202, a sequence of video frames is received. The sequence of video frames may be received from an imager or imaging system or may be received from a memory in which a previously generated sequence of video frames is stored. The sequence of video frames may be received frame-by-frame in a continuous fashion as the frames are generated (i.e., in real-time). In some examples, the sequence of video frames was captured during an endoscopic procedure, which may be an exploratory procedure, a diagnostic procedure, a study, a surgical procedure, a non-surgical procedure, an invasive procedure, or a non-invasive procedure.

At step 204, a brightness map is generated for each frame of the sequence of video frames received at step 202. The brightness map is generated based on a smoothing of regional brightness in the frame based on regional brightness gradients in the frame. The brightness of a region having relatively low gradients is smoothed while relatively large brightness gradients are preserved. The brightness map is a matrix of scaling weights corresponding to the pixels of the respective frame. Generally, each weight is computed based on a brightness gradient of a corresponding region of pixels of the respective frame. The weights corresponding to areas of low gradient are substantially similar, whereas weights corresponding to regions of strong gradient preserve a degree of the gradient structure.

Figure 3A:
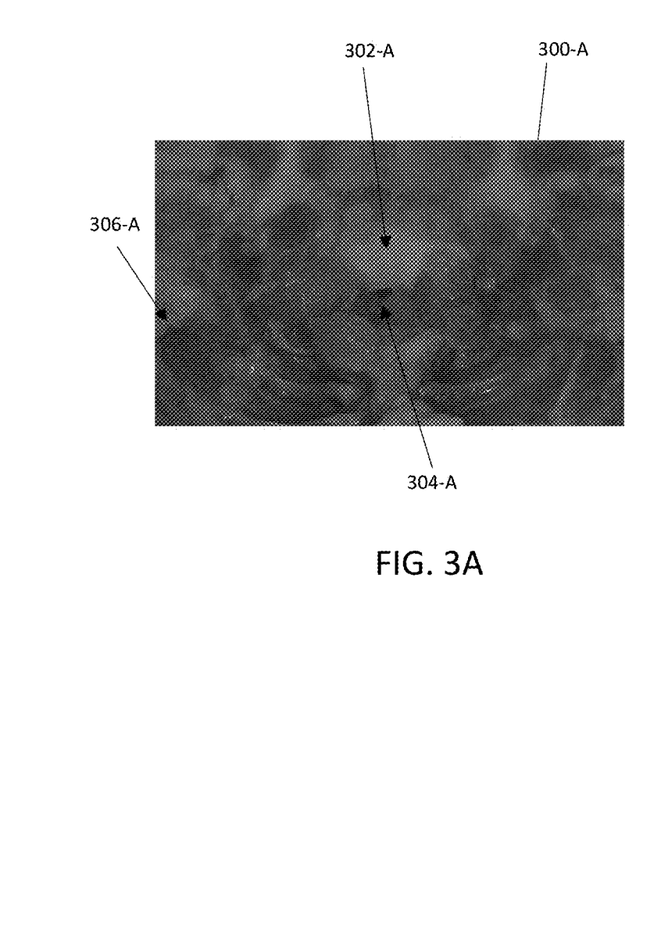
FIGS. 3A and 3B illustrate an example of a brightness map generated from a video frame.
Figure 3B:
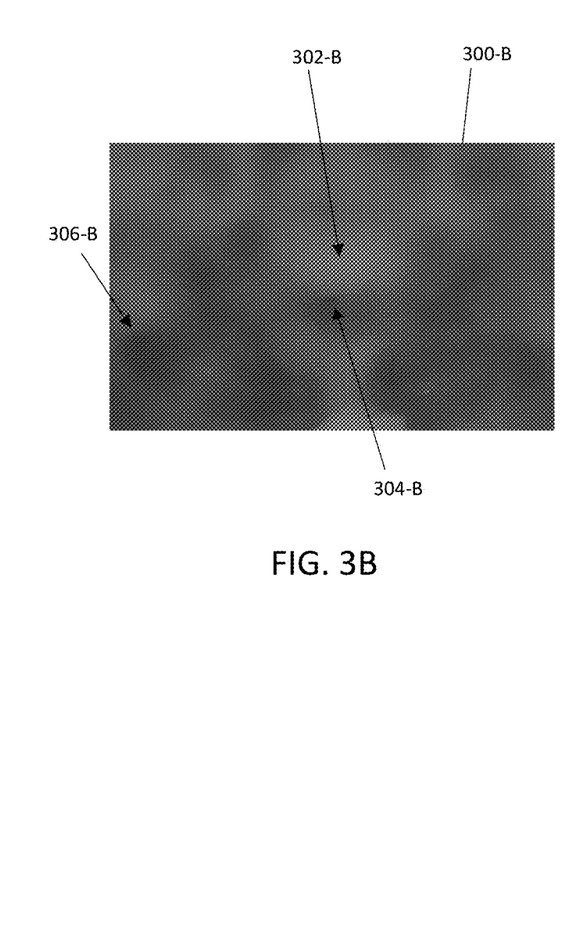

FIGS. 3A and 3B illustrate a brightness map generated from a video frame according to various examples of step 204. FIG. 3A is a video frame 300-A that is fairly dim, such as due to poor illumination of the field of view. FIG. 3B is a brightness map 300-B generated from the video frame of FIG. 3A. Comparing region 302-A in the video frame with region 302-B in the brightness map, it can be seen that the brightness in the brightness map is smoothed relative to the image frame with little to no texture from region 302-A being represented in 302-B. Since region 302-A in the video frame 300-A has relatively low brightness gradient, the resulting region 302-B in the brightness map 300-B has been smoothed However, while low brightness gradients are smoothed, high brightness gradients are still represented in the brightness map. For example, the small dark region 304-A in the video frame 300-A just beneath region 302-A is represented by region 304-B in the brightness map 300-B and the transition between the small dark region 304-A and the surrounding regions is still evident in the region 304-B and its surrounding regions in the brightness map 300-B. As another example, a relatively stark bright to dark transition in region 306-A in the video frame 300-A is represented in region 306-B in the brightness map 300-B. Thus, the brightness map 300-B preserves the stronger brightness-based "structural" aspects of video frame 300-A, while smoothing the more minor "textural" aspects of video frame 300-A.

Returning to FIG. 2, at step 206, an enhanced sequence of video frames is generated by adjusting pixel values of each frame based on the brightness map for the respective frame. A given pixel value is adjusted based on the corresponding scaling weight of the brightness map. The adjustment enhances brightness of relatively low brightness regions of the respective frame while not saturating regions of relatively high brightness regions. Due to the smoothing of regional brightness in the brightness map for low gradient regions, pixels within the low gradient regions are adjusted by similar scaling weights. But for pixels within the high gradient regions, the scaling weights will be different. Thus, the enhancement can be thought of as a gradient-based regional brightness enhancement. Since pixel values in a region of the video frame are adjusted together, finer ("textural") details and local contrast are preserved.

Adjustment of pixel values in step 206 is such that pixels in a region where the corresponding brightness map values are uniform will be adjusted by the same scaling weights. In some examples, the adjustment of pixel values in the video frames is inversely proportional to the brightness map such that pixel values corresponding to lower-brightness regions of the brightness map are increased more than pixel values corresponding to higher-brightness regions of the brightness map. In some examples, the same brightness map is used to adjust each color channel of the image.

Figure 4:
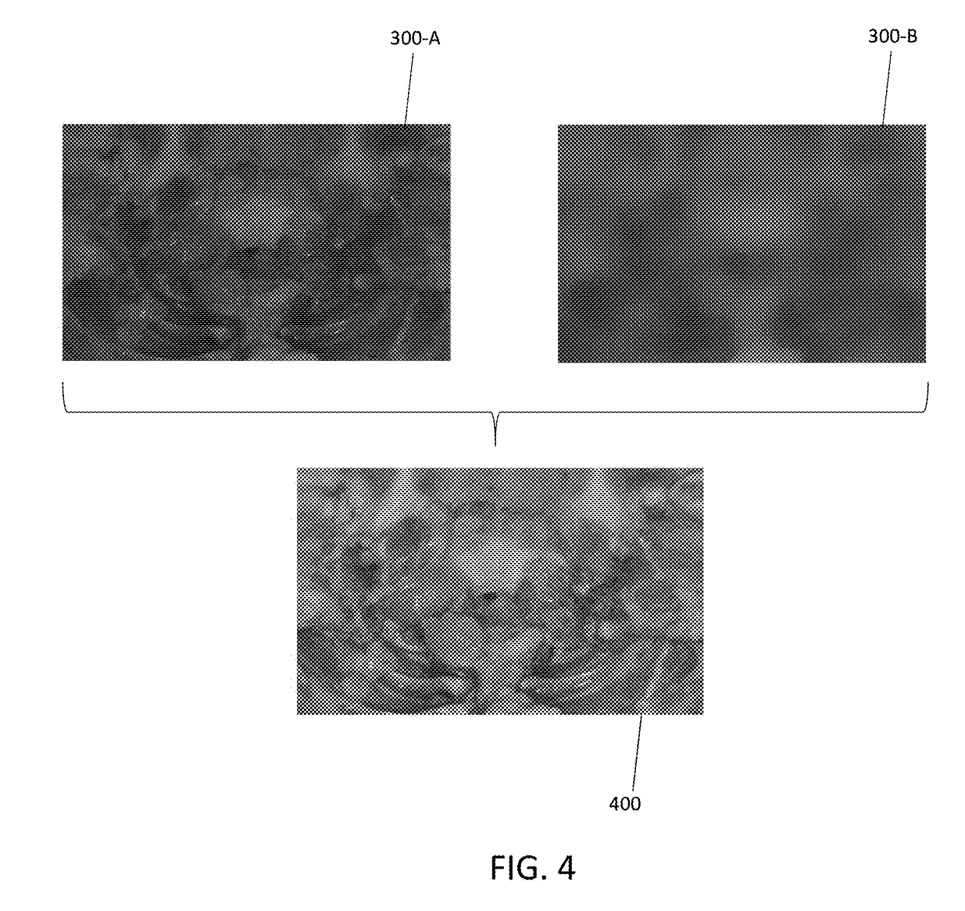
FIG. 4 illustrates an example of the creation of an enhanced frame from an original frame and a brightness map.

FIG. 4 illustrates an example of the creation of an enhanced frame 400 from the original frame 300-A and the brightness map 300-B from FIG. 3A and FIG. 3B. The brightness of the enhanced frame 400 is greater than that of the original frame 300-A, with more detail being evident due to the increased brightness. Comparing similar regions of the enhanced frame 400 with the brightness map 300-B, it is evident that the textural detail is preserved in the enhanced frame for regions where the brightness map has smoothed the brightness gradients. Moreover, it is evident that the brightness of darker regions of the original frame 300-A has been increased to a greater degree than the brightness of brighter regions.

At step 208, the enhanced sequence of video frames is displayed in real-time. In other words, the enhancement of the frames is performed as the frames are received. The enhanced frames can be displayed on a display screen during the imaging session, such as intra-operatively in the operating room to assist a surgeon in identifying tissue. In some examples, method 200 may be repeated for each frame in a sequence of video frames. For example, a series of video frames may be generated in real-time during an endoscopic procedure to assist a clinician in visualizing the tissue in the imaging field, and method 200 may be performed on each video frame as the frames are generated. Enhanced images may be generated and displayed as an enhanced video on a display screen to assist the clinician in visualizing the field of view.

Method 200 can include illuminating the tissue with illumination light, capturing the video frames, and transferring the captured video frames from the camera to a system for low-light enhancement of the frames, such as image processing unit 116 of FIG. 1. In some examples, video frames are analyzed to determine whether low-light image enhancement is needed such that method 200 is performed on an ad-hoc basis based on a determination that enhancement is needed. The determination can be made, for example, by image processing unit 116. In some examples, a user can command image enhancement, such as based on viewing frames that the user considers too dark. In some examples, method 200 is performed regardless of whether enhancement is subjectively needed, for example, because method 200 does not result in saturation and, therefore, poses little risk for image degradation.

One or more video frames generated by the imager can comprise an intensity value for each pixel of the imager. In some examples, the one or more video frames are based on frames generated by the imager. For example, one or more processing steps may be performed between the generation of the frames by the imager and the performance of step 202 of method 200. Examples of such processing steps include scaling, trimming, denoising, and normalizing. Accordingly, in some examples, the number of intensity values in the frame received at step 202 may be different than the number of pixels of the imager that generated the frame from which the received frame was derived. In some examples, one or more image processing steps may be performed after the frame is received at step 202. For example, generating the enhanced frame may include one or more of a scaling step, a trimming step, a denoising step, and a normalizing step.

Figure 5:
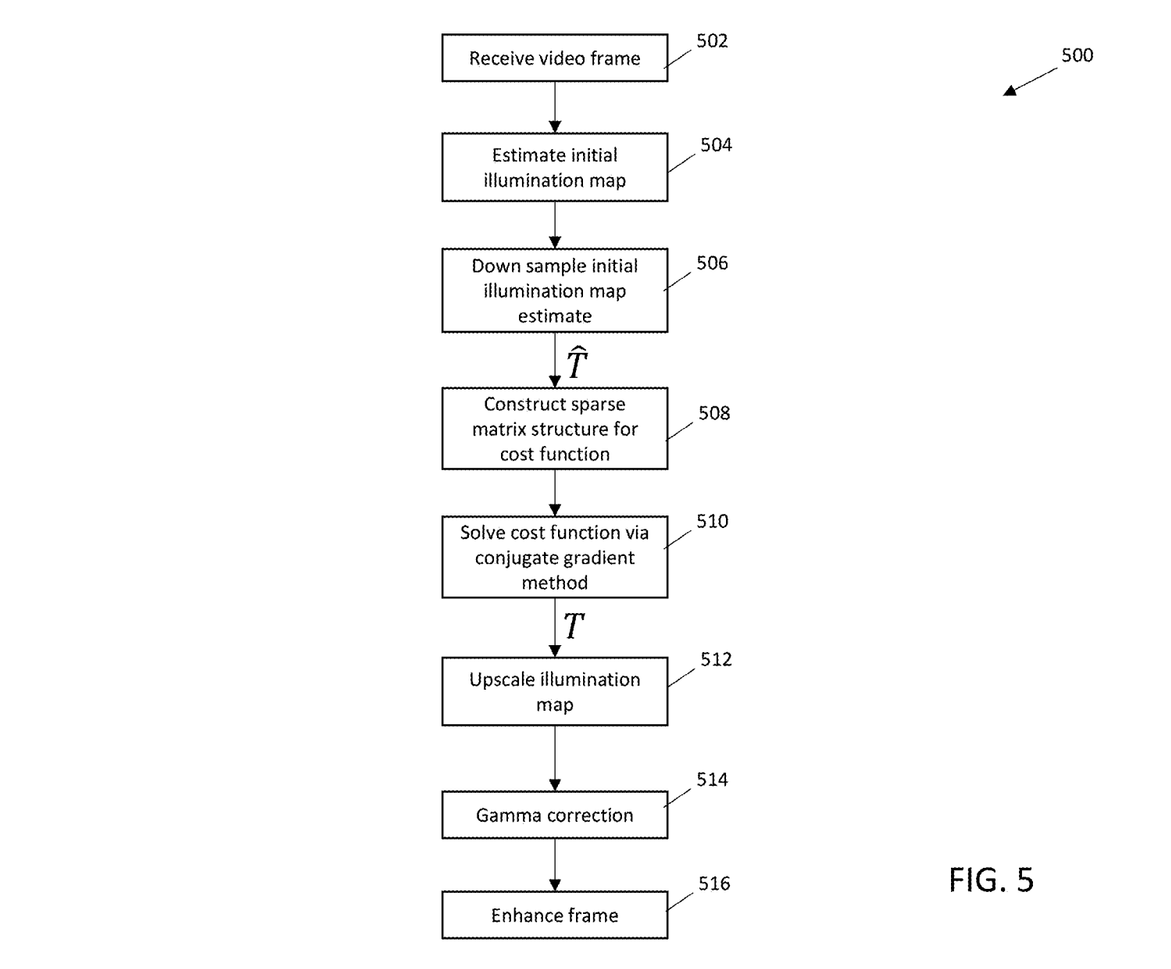
FIG. 5 illustrates an exemplary method for low-light image enhancement.

FIG. 5 illustrates an exemplary method 500 for low-light image enhancement, according to various aspects of method 200 of FIG. 2. As discussed further below, method 500 implements data conserving techniques to enable low-light image enhancement on high definition video in real-time.

Method 500 generates a brightness map by minimizing the following cost function:

$$\min_T \left( \|\hat{T} - T\|_F^2 + \alpha \sum_x \sum_{d \in \{h,v\}} W_d(x) \frac{(\nabla_d T(x))^2}{|\nabla_d \hat{T}(x)| + \varepsilon} \right) \quad (1)$$

T is the brightness map whose values are refined to minimize expression (1) and $\hat{T}$ is an initial brightness map estimation. The first term in expression (1) seeks to minimize the difference between the brightness map T and the initial brightness map estimate $\hat{T}$. The second term seeks to smooth areas of low brightness gradient, while preserving structure related to strong brightness gradients (e.g., edges). $\nabla_d \hat{T}(x)$ represents the gradient at pixel x in the initial brightness map estimate $\hat{T}$. $\nabla_d T(x)$ represents the gradient at pixel x in the brightness map T. $\varepsilon$ is a threshold value that is selected to distinguish strong gradient areas from low gradient areas (e.g., edges from non-edges). An exemplary value for $\varepsilon$ is 0.01. For areas with high gradients (e.g., strong edges), the gradient is much larger than $\varepsilon$, so $$\frac{(\nabla_d T(x))^2}{|\nabla_d \hat{T}(x)| + \varepsilon}$$

in equation (1) is approximately close to a constant (e.g. close to 1). In this case, T≈$\hat{T}$ and high gradients are preserved. For the areas with minor (textural) details, the gradients of both T and $\hat{T}$ are less than $\varepsilon$, and to minimize the cost function (1), the gradients of T could be minimized since the gradients of $\hat{T}$ are fixed. In this case, the local textural areas are smoothed and will have substantially consistent brightness level. Thus, expression (1) can provide a brightness map in which low brightness gradient areas are smoothed and strong gradients transitions are preserved.

In expression (1), $W_d(x)$ is a weight. Different weight strategies can be used. In some examples, $W_d(x)$ is a value of 1. In other examples, $W_d(x)$ is a function of $\hat{T}$, such as follows:

$$\frac{1}{|\nabla_d \hat{T}(x)| + \varepsilon}.$$

Expression (1) also includes weighting parameter $\alpha$, which is a predefined value. In some examples, $\alpha$ is in the range of 0.01 to 10.

Minimizing the cost function of expression (1) is equivalent to solving the following linear system (Ax=b):

$$\left( I + \sum_{d \in \{u,v\}} D_d^T \mathrm{Diag}(\tilde{w}_d) D_d \right) t = \hat{t} \quad (2)$$

Returning to FIG. 5, at step 502, a video frame is received. At step 504, an initial brightness map estimate $\hat{T}$ is generated. In some examples, the initial brightness map is the relative luminance of the video frame, calculated from the RGB values of the video frame, according to well-known methods. In some examples, the initial brightness map is the maximum value of the RGB values for a given pixel. In some examples, the initial brightness map value for a given pixel is based on the maximum value of a region of pixels centered on the given pixel.

At step 506, the initial brightness map estimate $\hat{T}$ is down sampled to reduce processing time in minimizing expression (1) since minimizing expression (1) for full-scale high resolution images (e.g., 2K and 4K resolution) may not be feasible in real-time on commercial image processing systems (e.g., even using processors tailored to image processing such as GPUs). In some examples, the brightness map initial brightness map estimate $\hat{T}$ is down sampled by a factor in the range from 0.1 to 0.5. In some examples, step 506 is not performed.

The matrix in equation (2) is a sparse matrix with dimension N×N, where N=R×C, and R is the row number and C is the column number of the image frame. For high resolution images, the size of this matrix presents a memory storage and/or processing challenge for solving equation (2) in a timely fashion, such as required for real-time processing. The inventors realized that there are only 5N non-zero elements in the sparse matrix. Hence, according to various examples, method 500 includes optional step 508 in which the sparse matrix structure of equation (2) can be constructed in a compressed sparse matrix structure. In some examples, the compressed sparse matrix structure is a compressed sparse row (CSR) format to store the non-zero elements only in the sparse matrix. In some examples, the CSR format includes: Row index vector of N+1 elements; Column index vector of 5N elements; and Non-zero values vector of 5N elements. Accordingly, only 11N+1 space may be required to store the N×N sparse matrix of equation (2), which represents a significant savings in stored and processed data so that equation (2) can be solved in real-time for high resolution video frames, according to various examples.

For example, given a small image with resolution 128× 128, the sparse matrix is 16384×16384, which even for the small image may be still too big to be stored in GPU memory. However, for this example with the CSR sparse matrix structure, only 11*16384+1 space is needed, which saves 99.93% of the memory required for the original matrix. Even compared with the coordinate list (COO) format ((row column, value) tuples with 15N spaces), it also saves 26.67% of the memory space.

In some examples, other sparse matrix structures may be used to reduce the storage space and processing time for solving equation (2), such as COO and compressed sparse column (CSC)

In some examples, once the sparse matrix structure of equation (2) is initialized (e.g., for the first frame in the series of video frames) in the CSR format, the row index and column index vectors are constant for all subsequent image frames. The only additional step is to update the non-zero values item in the structure based on the new frame. This could be used for estimating the brightness map directly, which can speed up the real-time processing.

At step 510, an iterative conjugate gradient method is used to solve the sparse linear system of equation (2) (with or without the compressed structure format of step 506). Since the matrix in equation (2) is a symmetric and positivedefinite sparse matrix, the solution t is unique. Therefore, a conjugate gradient method can be used to iteratively estimate the solution, such as on a parallel computing platform (e.g., a GPU). In some examples, leveraging the CSR storage format of step 506, the cuSparse and cuBLAS APIs in CUDA can be used to speed up the calculation in parallel for solving equation (2) in real-time, such as on a GPU. Step 510 provides the brightness map T.

At step 512, the brightness map is up-sampled if the initial brightness map estimate was down-sampled in step 506. In some examples, the brightness map is up-sampled to the original resolution via bilinear interpolation. In some variations, the brightness map may be up-sampled to the original resolution via bicubic interpolation or another interpolation method may be used for the up-sampling.

At optional step 514, a gamma correction is applied to the brightness map, with $T \leftarrow T^\gamma$. Any suitable value for $\gamma$ may be used, such as any value in the range of 0.1 to 1.0.

At step 516, the original video frame is enhanced via the brightness map (with or without the gamma correction). Each pixel of the original video frame is scaled according to the corresponding weight of the brightness map. In some examples, due to the brightness map smoothing small gradients, pixel values in a low gradient region may be scaled by equivalent or substantially equivalent weights even though the pixel values may be different. As such, areas are brightened as a region, which preserves detail. In some examples, the original video frame may be enhanced by dividing each pixel by the corresponding weight from the brightness map. In some examples, the same brightness map weight is used to adjust each color channel for each pixel of a color frame. In some examples, one or more additional post-processing steps may be performed, such as one or more denoising and/or recomposing steps which may be performed to produce the final enhanced frame.

Method 500 can be performed on each frame of a sequence of video frames to generate an enhanced sequence of video frames. In some examples, method 500 can be performed in real-time to generate enhanced video frames in real-time (i.e., at the same rate that the video frames are captured). In some examples, method 500 is performed via a parallel processing platform. In some examples, method 500 is performed on a GPU. In some examples, method 500 is performed on high resolution video frames (e.g., 2K, 4K, or higher resolution video frames).

Figure 6:
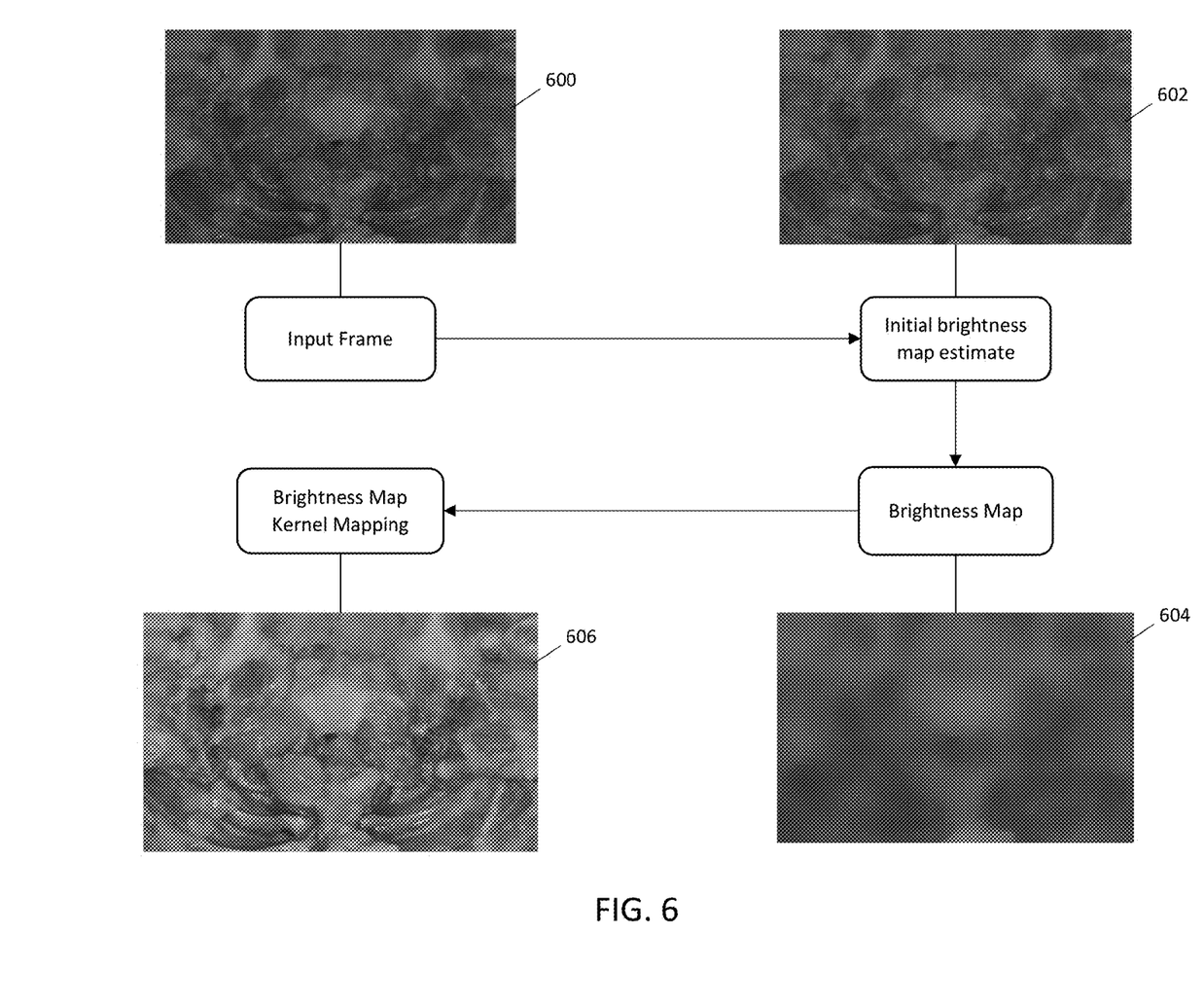
FIG. 6 illustrates an example of the results of various steps of the method of FIG. 5.

FIG. 6 illustrates an example of the results of various steps of method 500. The input frame 600 is used to generate an initial brightness map estimate 602, which as discussed above, can be a maximum value of the RGB channels for a respective pixel or the relative luminance Y for a respective pixel. A brightness map 604 is generated from the initial brightness map estimate 602, such as via solving equation (2) and using one or more of steps 506-514 of method 500. An enhanced frame 606 is generated from the brightness map 604 by scaling each pixel by the respective weight of the brightness map.

Figure 7:
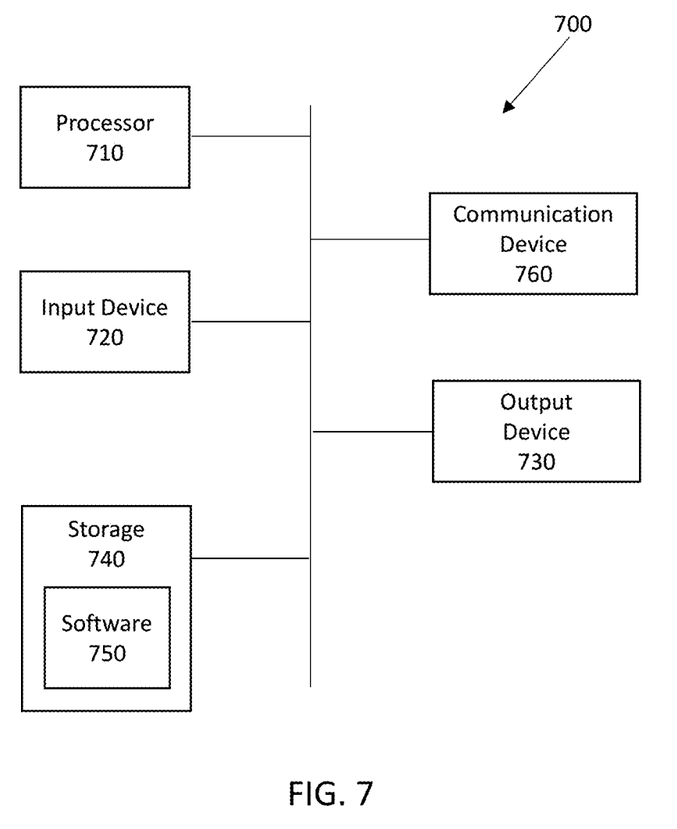
FIG. 7 illustrates an example of a computing system 700.

FIG. 7 illustrates an example of a computing system 700 that can be used for one or more of components of system 100 of FIG. 1, such as one or more of camera head 108, camera control unit 112, image processing unit 116, and illuminator 120. System 700 can be a computer connected to a network, such as one or more networks of hospital, including a local area network within a room of a medical facility and a network linking different portions of the medical facility. System 700 can be a client or a server. As shown in FIG. 7, system 700 can be any suitable type of processor-based system, such as a personal computer, workstation, server, handheld computing device (portable electronic device) such as a phone or tablet, or dedicated device. The system 700 can include, for example, one or more of input device 720, output device 730, one or more processors 710, storage 740, and communication device 760. Input device 720 and output device 730 can generally correspond to those described above and can either be connectable or integrated with the computer.

Input device 720 can be any suitable device that provides input, such as a touch screen, keyboard or keypad, mouse, gesture recognition component of a virtual/augmented reality system, or voice-recognition device. Output device 730 can be or include any suitable device that provides output, such as a display, touch screen, haptics device, virtual/augmented reality display, or speaker.

Storage 740 can be any suitable device that provides storage, such as an electrical, magnetic, or optical memory including a RAM, cache, hard drive, removable storage disk, or other non-transitory computer readable medium. Communication device 760 can include any suitable device capable of transmitting and receiving signals over a network, such as a network interface chip or device. The components of the computing system 700 can be connected in any suitable manner, such as via a physical bus or wirelessly.

Processor(s) 710 can be any suitable processor or combination of processors, including any of, or any combination of, a central processing unit (CPU), graphics processing unit (GPU), field programmable gate array (FPGA), and application-specific integrated circuit (ASIC). Software 750, which can be stored in storage 740 and executed by one or more processors 710, can include, for example, the programming that embodies the functionality or portions of the functionality of the present disclosure (e.g., as embodied in the devices as described above). For example, software 750 can include one or more programs for execution by one or more processor(s) 710 for performing one or more of the steps of method 200 and/or method 500.

Software 750 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 740, that can contain or store programming for use by or in connection with an instruction execution system, apparatus, or device.

Software 750 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 700 can implement any operating system suitable for operating on the network. Software 750 can be written in any suitable programming language, such as C, C++, Java, or Python. In various examples, application software embodying the functionality of the present disclosure can be deployed in different configurations, such as in a client/server arrangement or through a Web browser as a Web-based application or Web service, for example.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for enhancing low brightness regions in endoscopic video comprising:
  receiving a sequence of video frames captured during an endoscopic procedure;
  generating a brightness map for each frame of the sequence of video frames, wherein the brightness map is generated based on smoothing regional brightness in the respective frame based on regional brightness gradients, and wherein the brightness map for the respective frame comprises scaling weights corresponding to pixels of the respective frame;
  generating in real-time an enhanced sequence of video frames as the sequence of video frames is received during the endoscopic procedure by adjusting pixel values of each frame of the sequence of video frames by scaling the pixel values of the respective frame by the scaling weights of the brightness map for the respective frame to enhance brightness of low brightness regions of the respective frame; and
  displaying the enhanced sequence of video frames to a surgeon in real-time during the endoscopic procedure.

2. The method of claim 1, wherein the enhanced sequence of video frames is generated in real-time by a graphics processing unit (GPU).

3. The method of claim 1, comprising down-sampling the respective frame and generating the respective brightness map based on the down-sampling of the respective frame.

4. The method of claim 3, comprising up-sampling the respective brightness map and adjusting the pixel values of the respective frame based on the up-sampling of the respective brightness map.

5. The method of claim 4, wherein the respective brightness map is up-sampled using bilinear interpolation.

6. The method of claim 1, wherein generating the brightness map for each frame of the sequence of video frames comprises minimizing a cost function, wherein the cost function comprises a sparse matrix and minimizing the cost function comprises constructing a compressed sparse matrix structure.

7. The method of claim 6, wherein the compressed sparse matrix structure is constructed in compressed sparse row format.

8. The method of claim 6, wherein the compressed sparse matrix structure includes a row index vector, a column index vector, and a non-zero values vector, the row index vector and column index vector are the same for each frame, and constructing the sparse matrix structure comprises updating the non-zero values vector for the respective frame.

9. The method of claim 6, comprising using an iterative conjugate gradient method to solve the minimization of the cost function.

10. The method of claim 1, wherein each of the scaling weights is computed based on a brightness gradient of a corresponding region of pixels of the respective frame.

11. The method of claim 10, wherein adjusting the pixel values of each of the frames comprises scaling the pixel values by the weights of the matrix of weights.

12. The method of claim 10, wherein each of the frames comprises different color channels and adjusting pixel values of each of the frames comprises scaling each of the color channels of a given pixel by the same weight.

13. The method of claim 1, comprising, prior to generating a brightness map for each frame of the sequence of video frames: generating an initial brightness map estimate for each frame of the sequence of video frames; and down-sampling the initial brightness map estimate for each frame of the sequence of video frames.

14. The method of claim 13, wherein the brightness map for each frame of the sequence of video frames is generated based on the respective down-sampled initial brightness map estimate.

15. A system comprising one or more processors, memory, and one or more programs stored in the memory for execution by the one or more processors for:
  receiving a sequence of video frames captured during an endoscopic procedure;
  generating a brightness map for each frame of the sequence of video frames, wherein the brightness map is generated based on smoothing regional brightness in the respective frame based on regional brightness gradients, and wherein the brightness map for the respective frame comprises scaling weights corresponding to pixels of the respective frame;
  generating in real-time an enhanced sequence of video frames as the sequence of video frames is received during the endoscopic procedure by adjusting pixel values of each frame of the sequence of video frames by scaling the pixel values of the respective frame by the scaling weights of the brightness map for the respective frame to enhance brightness of low brightness regions of the respective frame; and
  displaying the enhanced sequence of video frames to a surgeon in real-time during the endoscopic procedure.

16. The system of claim 15, wherein the enhanced sequence of video frames is generated in real-time by a graphics processing unit (GPU).

17. The system of claim 15, wherein the one or more programs include instructions for down-sampling the respective frame and generating the respective brightness map based on the down-sampling of the respective frame.

18. The system of claim 17, wherein the one or more programs include instructions for up-sampling the respective brightness map and adjusting the pixel values of the respective frame based on the up-sampling of the respective brightness map.

19. The system of claim 18, wherein the respective brightness map is up-sampled using bilinear interpolation.

20. The system of claim 15, wherein generating the brightness map for each frame of the sequence of video frames comprises minimizing a cost function, wherein the cost function comprises a sparse matrix and minimizing the cost function comprises constructing a compressed sparse matrix structure.

21. The system of claim 20, wherein the compressed sparse matrix structure is constructed in compressed sparse row format.

22. The system of claim 20, wherein the compressed sparse matrix structure includes a row index vector, a column index vector, and a non-zero values vector, the row index vector and column index vector are the same for each frame, and constructing the sparse matrix structure comprises updating the non-zero values vector for the respective frame.

23. The system of claim 20, wherein the minimization of the cost function is solved via an iterative conjugate gradient method.

24. The system of claim 15, wherein each of the scaling weights is computed based on a brightness gradient of a corresponding region of pixels of the respective frame.

25. The system of claim 24, wherein adjusting the pixel values of each of the frames comprises scaling the pixel values by the weights of the matrix of weights.

26. The system of claim 24, wherein each of the frames comprises different color channels and adjusting pixel values of each of the frames comprises scaling each of the color channels of a given pixel by the same weight.

27. The system of claim 15, wherein the one or more programs include instructions for, prior to generating a brightness map for each frame of the sequence of video frames: generating an initial brightness map estimate for each frame of the sequence of video frames; and down-sampling the initial brightness map estimate for each frame of the sequence of video frames.

28. The system of claim 27, wherein the brightness map for each frame of the sequence of video frames is generated based on the respective down-sampled initial brightness map estimate.

29. A non-transitory computer readable medium comprising instructions for execution by one or more processors of a system to cause the system to:
receive a sequence of video frames captured during an endoscopic procedure;
generate a brightness map for each frame of the sequence of video frames, wherein the brightness map is generated based on smoothing regional brightness in the respective frame based on regional brightness gradients, and wherein the brightness map for the respective frame comprises scaling weights corresponding to pixels of the respective frame;
generate in real-time an enhanced sequence of video frames as the sequence of video frames is received during the endoscopic procedure by adjusting pixel values of each frame of the sequence of video frames by scaling the pixel values of the respective frame by the scaling weights of the brightness map for the respective frame to enhance brightness of low brightness regions of the respective frame; and
display the enhanced sequence of video frames to a surgeon in real-time during the endoscopic procedure.

* * * * *